United States Patent
Damaskinos et al.

(10) Patent No.: US 9,632,301 B2
(45) Date of Patent: Apr. 25, 2017

(54) SLIDE SCANNER WITH A TILTED IMAGE

(71) Applicant: Huron Technologies International Inc., Waterloo (CA)

(72) Inventors: Savvas Damaskinos, Kitchener (CA); Arthur Edward Dixon, Waterloo (CA)

(73) Assignee: Huron Technologies International Inc., Waterloo (CA)

( * ) Notice: Subject to any disclaimer, the term of this patent is extended or adjusted under 35 U.S.C. 154(b) by 316 days.

(21) Appl. No.: 14/346,661

(22) PCT Filed: Sep. 21, 2012

(86) PCT No.: PCT/CA2012/000868
§ 371 (c)(1),
(2) Date: Mar. 21, 2014

(87) PCT Pub. No.: WO2013/040686
PCT Pub. Date: Mar. 28, 2013

(65) Prior Publication Data
US 2014/0231638 A1 Aug. 21, 2014

Related U.S. Application Data

(60) Provisional application No. 61/537,460, filed on Sep. 21, 2011.

(51) Int. Cl.
*G02B 7/04* (2006.01)
*G02B 21/06* (2006.01)
*B82Y 35/00* (2011.01)
*G02B 21/00* (2006.01)
*G01N 21/64* (2006.01)
*G02B 21/16* (2006.01)
*G02B 21/34* (2006.01)
*G02B 21/36* (2006.01)

(52) U.S. Cl.
CPC .............. *G02B 21/06* (2013.01); *B82Y 35/00* (2013.01); *G01N 21/6456* (2013.01); *G02B 21/002* (2013.01); *G02B 21/16* (2013.01); *G02B 21/34* (2013.01); *G02B 21/367* (2013.01)

(58) Field of Classification Search
CPC ...... G01B 9/04; G06K 9/00134; G02B 21/06; G02B 21/34; G02B 21/367
USPC ........................ 250/234, 201.3; 359/363, 383
See application file for complete search history.

(56) References Cited

U.S. PATENT DOCUMENTS

2009/0231689 A1* 9/2009 Pittsyn ..................... G01B 9/04
359/363

* cited by examiner

*Primary Examiner* — Thanh Luu
(74) *Attorney, Agent, or Firm* — Daryl W. Scnurr

(57) ABSTRACT

An instrument and method for scanning a large microscope specimen uses a light source and at least one lens to focus light from the specimen onto a detector array. The specimen holder is located on a scanning stage and the detector array is dynamically tilted about a scan direction during the scan to maintain focus across the width of the scan strip as the scan proceeds. A degree of tilt varies during the scan as is required to maintain lateral focus relative to the detector array.

22 Claims, 6 Drawing Sheets

SLIDE SCANNER WITH A TILTED IMAGE

BACKGROUND OF THE INVENTION

Field of the Invention

This invention relates to the fields of microscopic imaging of large specimens with particular emphasis on brightfield and fluorescence imaging. Applications include imaging tissue specimens, genetic microarrays, protein arrays, tissue arrays, cells and cell populations, biochips, arrays of biomolecules, detection of nanoparticles, photoluminescence imaging of semiconductor materials and devices, and many others.

Description of the Prior Art

Several technologies are used for imaging large specimens at high resolution. Tiling microscopes record an image of a small area of the specimen using a digital camera (usually a CCD camera), the specimen is moved with a computer-controlled microscope stage to image an adjacent area, an image of the adjacent area is recorded, the stage is moved again to the next area, and so on until a number of image tiles have been recorded that together cover the whole area of the specimen. Images of each area (image tiles) are recorded when the stage is stationary, after waiting long enough for vibrations from the moving stage to dissipate, and using an exposure time that is sufficient to record the fluorescence images. These image tiles can be butted together, or overlapped and stitched using computer stitching algorithms, to form one image of the entire specimen. Such images may contain tiling artifacts caused by different focus positions for adjacent tiles. For large specimens, thousands of tiles may be required to image the entire specimen, requiring many changes in focus which increase the chances of tiling artifacts.

Strip scanning instruments are often used for imaging large specimens on microscope slides. In these instruments infinity-corrected microscope optics are used, with a high Numerical Aperture (high NA) microscope objective and a tube lens of the appropriate focal length to focus an image of the specimen directly onto a CCD or CMOS linear array sensor or TDI sensor, and with the correct magnification to match the resolution of the microscope objective with the detector pixel size for maximum magnification in the digitized image {as described in "Choosing Objective Lenses: The Importance of Numerical Aperture and Magnification in Digital Optical Microscopy", David W. Piston, Biol. Bull. 195, 1-4 (1998)}. A linear CCD detector array with 1000 or 2000 pixels is often used, and three separate linear detectors with appropriate filters to pass red, green and blue light are used for RGB brightfield imaging. A high Numerical Aperture 20× microscope objective is often used, with a 1 mm field of view. The sample is moved at constant speed in the direction perpendicular to the long dimension of the linear detector array to scan a narrow strip across a microscope slide. The entire slide can be imaged by imaging repeated strips and butting them together to create the final image. Another version of this technology uses TDI (Time Delay and Integration) array sensors which increase both sensitivity and imaging speed. In both of these instruments, exposure is varied by changing illumination intensity and/or scan speed.

Such a microscope is shown in FIG. 1 (Prior Art). A tissue specimen 100 (or other specimen to be imaged) mounted on microscope slide 101 is illuminated from below by illumination source 110. Light passing through the specimen is collected by infinity-corrected microscope objective 115 which is focused on the specimen by piezo positioner 120. The microscope objective 115 and tube lens 125 form a real image of the specimen on linear detector array 130. An image of the specimen is collected by moving the microscope slide at constant speed in scan direction 102 along the Y direction using motorized stage 105 in a direction perpendicular to the long dimension of the detector array 130, combining a sequence of equally-spaced line images from the array to construct an image of one strip across the specimen. Strips are then assembled to form a complete image of the specimen.

For brightfield imaging, most strip-scanning instruments illuminate the specimen from below, and detect the image in transmission using a sensor placed above the specimen. In brightfield, signal strength is high, and red, green and blue channels are often detected simultaneously with separate linear detector arrays to produce a colour image.

A prior art scanning microscope for fluorescence imaging is shown in FIG. 2. A tissue specimen 100 (or other specimen to be imaged) mounted on microscope slide 101 is illuminated from above by illumination source 200. In fluorescence imaging, the illumination source is usually mounted above the specimen (epifluorescence) so that the intense illumination light that passes through the specimen is not mixed with the weaker fluorescence emission from the specimen, as it would be if the illumination source were below the specimen. Several different optical combinations can be used for epifluorescence illumination—including illumination light that is injected into the microscope tube between the microscope objective and the tube lens, using a dichroic beamsplitter to reflect it down through the microscope objective and onto the specimen. In addition, a narrow wavelength band for the illumination light is chosen to match the absorption peak of the fluorophore in use. Fluorescence emitted by the specimen is collected by infinity-corrected microscope objective 115 which is focused on the specimen by piezo positioner 120. Emission filter 205 is chosen to reject light at the illumination wavelength and to pass the emission band of the fluorophore in use. The microscope objective 115 and tube lens 125 form a real image of the specimen on TDI detector array 210. An image of the specimen is collected by moving the microscope slide at constant speed in scan direction 102 along the Y direction using motorized stage 105 in a direction perpendicular to the long dimension of the detector array 210, combining a sequence of equally-spaced, time-integrated line images from the array to construct an image of one strip across the specimen. Strips are then assembled to form a complete image of the specimen. When a CCD-based TDI array is used, each line image stored in memory is the result of integrating the charge generated in all of the previous lines of the array while the scan proceeds, and thus has both increased signal/noise and amplitude (due to increased exposure time) when compared to the result if a linear array detector were used.

A description of strip scanning instruments, using either linear arrays or TDI arrays, is given in US Patent Application Publication # US2009/0141126 A1 ("Fully Automatic Rapid Microscope Slide Scanner", by Dirk Soenksen).

When either linear arrays or TDI arrays are used for scanning a tissue specimen, focus is maintained along the scan strip by moving microscope objective 115 with piezo positioner 120. A focus map for each strip is created before scanning with measurements at several positions along the strip and focus is maintained by the piezo positioner in accordance with the focus map; or automatic focus is achieved during scanning using a separate detector or focus-measuring device. The measurement of best focus position for autofocusing a point scanner (or one using a linear array detector) was described in "Autofocusing for wide field-of-view laser scanning imaging systems", G. Li, S. Damaskinos & A. Dixon, Scanning 28(2), 74-75 (2006). This paper describes the use of an X-Z image acquired at each of several focus points on the specimen to produce a best focus position by segmenting the X-Z image along X and calculating a best focus position for each segment. The result of a best linear fit for these focus positions is used as the line of best focus. In the Y direction, the best focus is determined by a best linear fit to focus positions calculated for various Y locations. Spatial domain intensity gradient-based solutions were found to work better than spatial frequency domain-based solutions.

If the specimen is not flat, or the specimen is tilted about the scan direction, proper focus may not be achieved across the whole width of the strip. In addition, focus at the edge of adjacent strips may be different, making it difficult to stitch image strips together to assemble a complete image of the specimen without focus mismatch at the edge of strips. These problems are made worse when magnification is increased (which decreases depth of field) and when the width of the scan strip on the specimen is increased.

Definitions

For the purposes of this patent document, a "large microscope specimen" (or "macroscopic specimen") is defined as one that is larger than the field of view of a compound optical microscope containing a microscope objective that has the same Numerical Aperture (NA) as that of the scanner described in this document.

For the purposes of this patent document, "TDI" or "Time Delay and Integration" is defined as the method and detectors used for scanning moving objects consisting of a CCD- or CMOS-based TDI detector array and associated electronics. In a CCD-based TDI array, charge is transferred from one row of pixels in the detector array to the next in synchronism with the motion of the real image of the moving object. As the object moves, charge builds up and the result is charge integration just as if a longer exposure were used to image a stationary object. When an object position in the moving real image (and integrated charge) reaches the last row of the array, that line of pixels is read out. In operation, the image of the moving specimen is acquired one row at a time by sequentially reading out the last line of pixels on the detector. This line of pixels contains the sum of charge transferred from all previous lines of pixels collected in synchronism with the image moving across the detector. One example of such a camera is the DALSA Piranha TDI camera. In a CMOS-based TDI detector, voltage signals are transferred instead of charge.

For the purposes of this patent document, a "frame grabber" is any electronic device that captures individual, digital still frames from an analog video signal or a digital video stream or digital camera. It is often employed as a component of a computer vision system, in which video frames are captured in digital form and then displayed, stored or transmitted in raw or compressed digital form. This definition includes direct camera connections via USB, Ethernet, IEEE 1394 ("FireWire") and other interfaces that are now practical.

For the purposes of this patent document, "depth of focus" of a microscope is defined as the range the image plane can be moved while acceptable focus is maintained, and "depth of field" is the thickness of the specimen that is sharp at a given focus level. "Depth of focus" pertains to the image space, and "depth of field" pertains to the object (or specimen) space.

For the purposes of this patent document, "fluorescence" includes single-photon and multi-photon excitation, and photoluminescence; and "specimen" includes, but is not limited to, tissue specimens, genetic microarrays, protein arrays, tissue arrays, cells and cell populations, biochips, arrays of biomolecules, plant and animal material, insects and semiconductor materials and devices. Specimens may be mounted on or contained in any kind of specimen holder.

The "scan plane" is a plane perpendicular to the optical axis of the instrument in which the specimen is moved by the moving specimen stage. When the specimen is mounted on a microscope slide, the scan plane is parallel to the surface of the microscope slide, unless the slide is tilted with respect to the moving specimen stage.

An "object plane" is a plane in the specimen (often just below the surface) that corresponds to an "image plane" on which a real image of the object plane is formed, and on which the detector is situated. An "object line" is a line in the object plane which corresponds to an "image line" (a line in the "image plane") on which a real image of the object line is formed, and on which a linear detector is situated. The image detected by this linear detector is a "line image".

"Dynamic tilt" is defined as tilting the detector about the scan direction in order to maintain lateral focus across the width of a scan strip during a scan, where the degree of tilt varies during the scan to maintain lateral focus.

The "scan direction" is the direction of stage motion during scanning (the Y-direction in all diagrams).

OBJECTS OF THE INVENTION

1. It is an object of this invention to provide an instrument and method of scanning a large microscope specimen on a glass microscope slide (or other specimen holder) using a linear detector array that can be dynamically tilted about the scan direction during scan such that focus can be maintained across the width of the scan strip as the scan proceeds.
2. It is an object of this invention to provide an instrument and method of scanning a large microscope specimen on a glass microscope slide (or other specimen holder) for fluorescence imaging using a TDI detector array that can be dynamically tilted about the scan direction during scan such that focus can be maintained across the width of the scan strip as the scan proceeds.
3. It is an object of this invention to provide an instrument and method of scanning a large microscope specimen on a glass microscope slide (or other specimen holder) for fluorescence imaging using a 2D detector array that can be dynamically tilted about the scan direction during scan and Moving Specimen Image Averaging such that focus can be maintained across the width of the scan strip as the scan proceeds.
4. It is an object of this invention to provide a method of measuring the focus and tilt required before scanning to maintain focus relative to the specimen and across the width of the scan strip as the scan proceeds.

BRIEF DESCRIPTION OF THE DIAGRAMS

DESCRIPTION OF THE INVENTION

Figure 1:
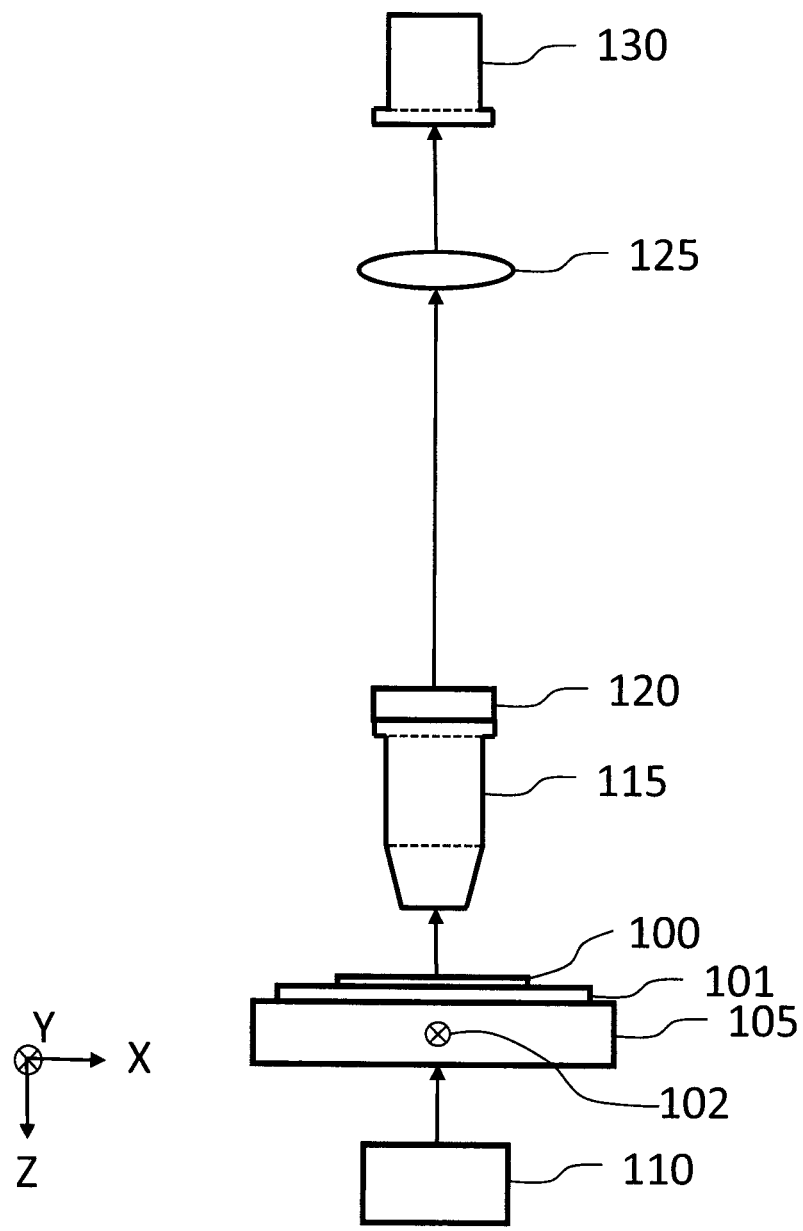
FIG. 1 is a schematic view of a prior-art brightfield microscope slide scanner using a linear detector array.
Figure 2:
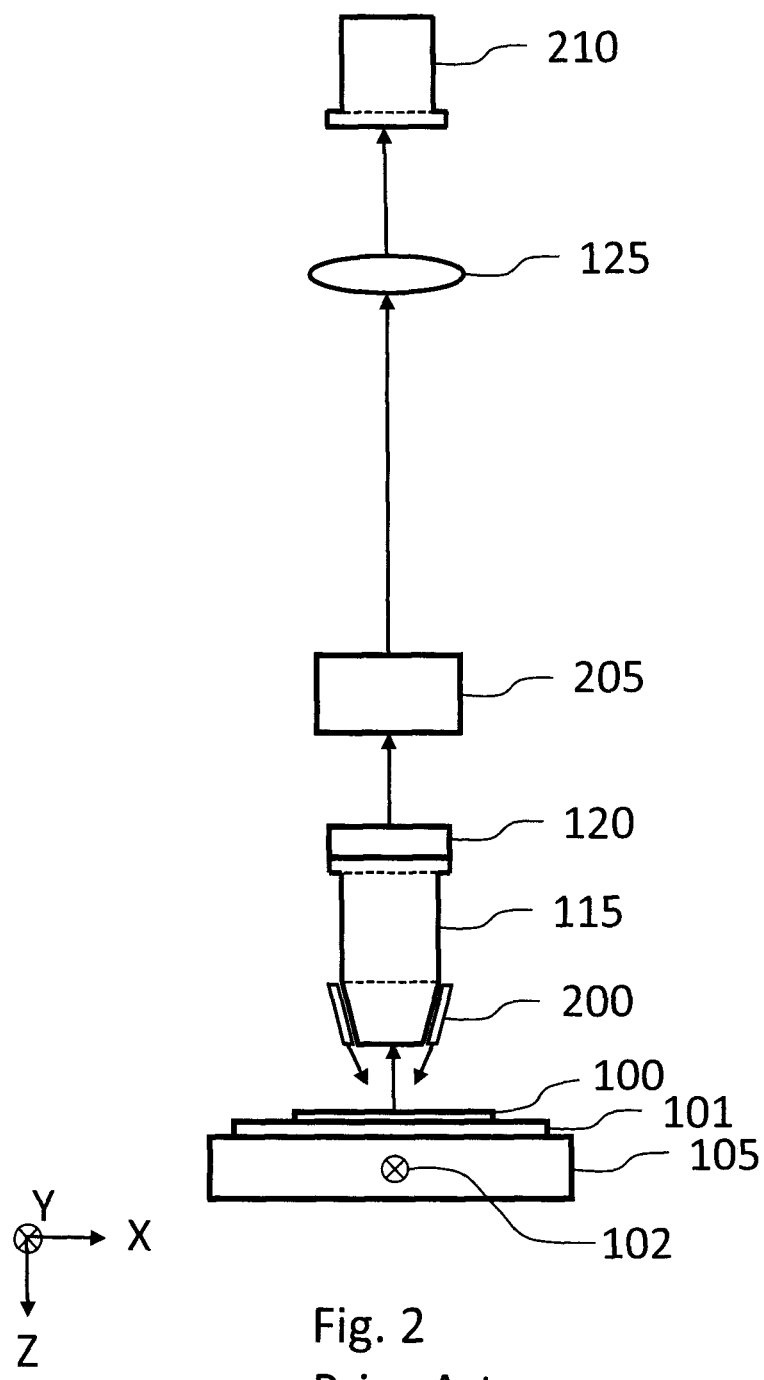
FIG. 2 is a schematic view of a prior-art fluorescence microscope slide scanner using a TDI detector array.
Figure 3:
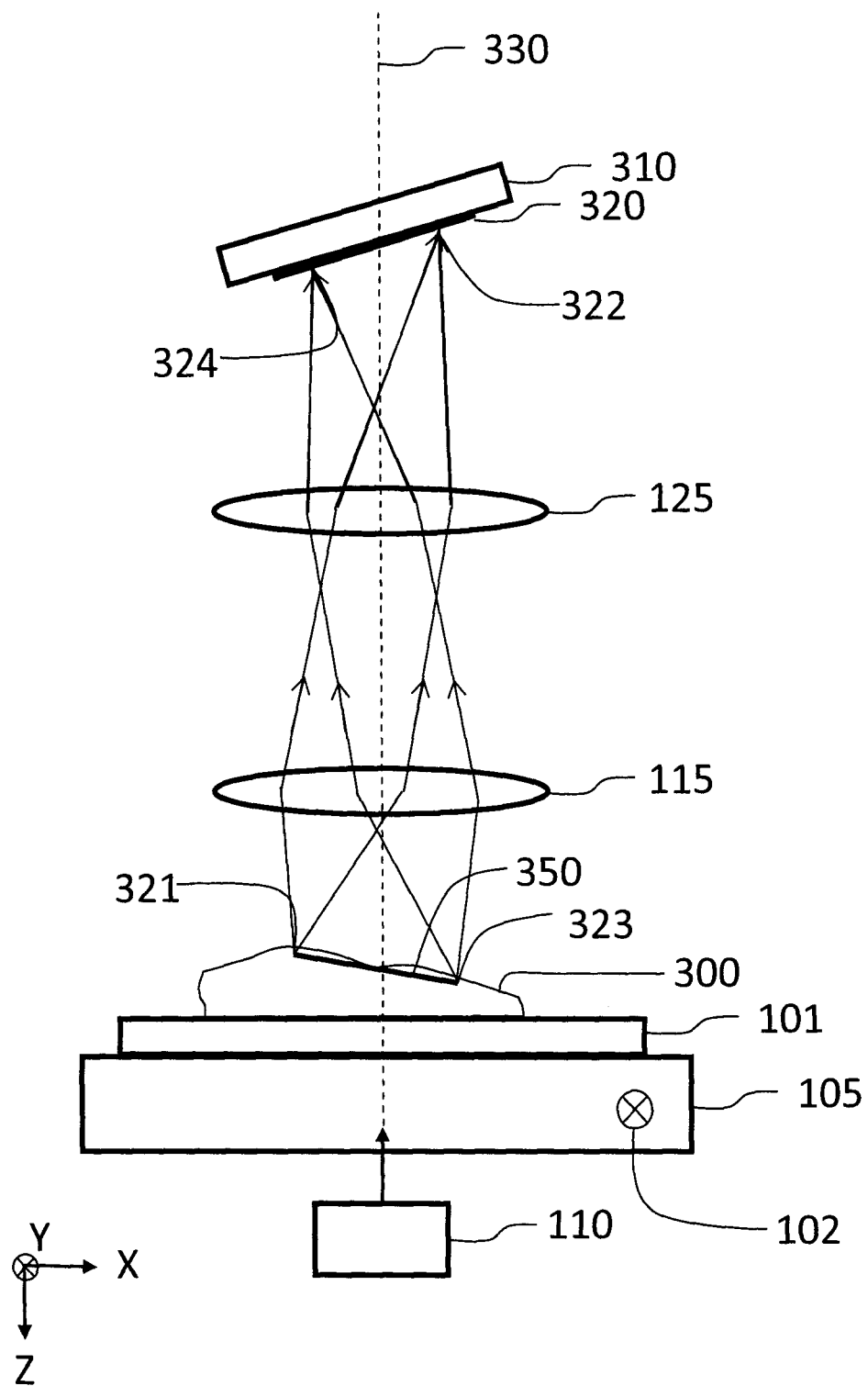
FIG. 3 is a schematic view of a brightfield scanner using a detector array tilted about the scan direction, showing how this results in an object plane that is also tilted about the scan direction.

FIG. 3 shows a slide scanner for transmission imaging that is a first embodiment of this invention. A tissue specimen 300 (or other specimen to be imaged) is mounted on microscope slide 101 (or other sample holder) on a scanning stage 105. For transmission imaging, the specimen is illuminated from below by light source 110. Microscope objective 115 (or other imaging objective) and tube lens 125 focus light from the specimen onto linear detector array 310, which is tilted with respect to the scan plane about an axis (the Y axis) that is in the plane of the microscope slide and is parallel to the direction of stage motion 102 (along the Y direction), and is perpendicular to the row of pixels along the long dimension of the array. When focused by lens 125, light from tilted object line 350 in specimen 300 is collected by the row of detector pixels in image line 320 in linear array detector 310. Light from specimen 300 at position 321 will be focused on a pixel at position 322 on image line 320, and light from the specimen at position 323 will be focused on a pixel at position 324 on image line 320. Each pixel in detector 310 collects data from a different position on tilted object line 350. Light source 110, microscope objective 115, tube lens 125, and detector 310 are situated on the optical axis 330 of the instrument. This diagram shows the standard infinity-corrected microscope configuration comprised of microscope objective 115 and tube lens 125. However, a simpler optical train using only a single objective lens focusing light from the specimen directly onto the linear array detector is also possible. In FIG. 3, as in FIG. 1, axial focus (focus in the Z direction) is achieved by moving microscope objective 115 in the Z direction using piezo positioner 120 (not shown in FIG. 3). Alternatively, either specimen 300 or detector 310 can be moved in the Z direction to achieve axial focus. In this first embodiment, motion of the scanning stage 105, focus motion of objective 115, and dynamic tilt of array detector 310 are computer controlled (see FIG. 4).

Figure 4:
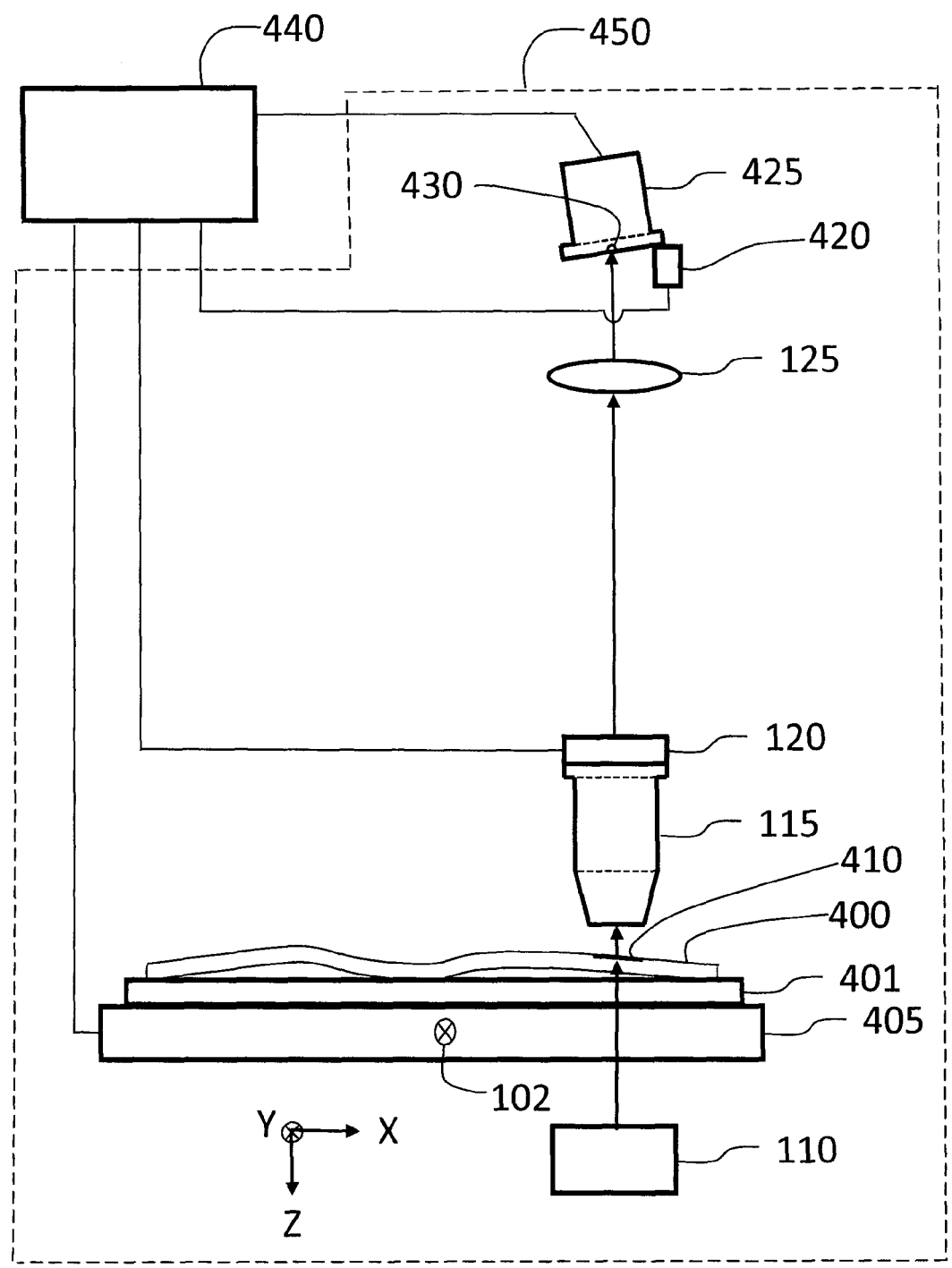
FIG. 4 is a schematic view of a brightfield scanner with a detector array tilted about the scan direction.

FIG. 4 shows a slide scanner 450 for transmission imaging that is a second embodiment of this invention. A tissue specimen 400 (or other specimen to be imaged) mounted on microscope slide 401 is illuminated from below by illumination source 110. Light passing through the specimen is collected by infinity-corrected microscope objective 115 which is focused on the specimen by piezo positioner 120 (or other focusing mechanism). The microscope objective 115 and tube lens 125 form a real image of the specimen on linear detector array 425, which can be tilted about tilt axis 430 using piezoelectric pusher 420 (or other tilt mechanism). The long dimension of linear detector array 425 is perpendicular to scan direction 102. Tilt axis 430 is parallel to scan direction 102. An image of the specimen is collected by moving the microscope slide at constant speed using motorized stage 405 in a direction perpendicular to the long dimension of the detector array 425, combining a sequence of equally-spaced line images from the array to construct an image of one strip across the specimen, with strip width equal to the length of object line 410. When one strip is imaged, motorized stage 405 moves the specimen in the X direction a distance equal to the strip width, and a second strip is scanned. This procedure is repeated until the entire area of the specimen (or the area of interest) has been scanned. Strips are then assembled to form a complete image. Computer 440 controls motorized stage 405, piezoelectric pusher 420, and piezo positioner 120, and collects data from detector array 425. In addition to controlling all of the electromechanical parts of the scanner 450, the computer 440 also performs all of the other functions necessary to acquire, store, process and display digital image data.

Note that all scanners described in FIGS. 3 to 6 of this patent document are computer-controlled, and use a computer programmed to acquire, store, process and display digital image data. Except for FIG. 4, the computer portion of these instruments is not shown in the diagrams. Preferably, a computer is programmed and configured to vary a degree of tilt of the detector array dynamically during the scan about the scan direction in order to maintain the focus relative to the specimen.

In prior-art scanners, several focus positions are measured along each strip before scanning, and a focus map is produced to enable dynamic focus during scanning using piezo positioner 120 to move microscope objective 115 under computer control. When a specimen is not flat, like tissue specimen 400, it is important to maintain focus across the width of each strip (strip width 400 in this diagram) and also to make sure that the edges of adjacent strips have the same focus inside the specimen. This is important because if the edges of adjacent strips are focused at a different depth inside the specimen, it is difficult to match the image data at the edge of the strips, and an image artifact results. Matching is sometimes done by simply butting together strip edges, which requires precision knowledge of pixel positions in each strip, or by overlapping adjacent strips and using a feature-matching algorithm to align the two images. In either case, if the focus positions of the two strip edges are different, an image artifact can result in the final image. The present invention has two important advantages over prior-art scanners: tilting the detector about the scan direction makes it possible to maintain focus across the width of the strip, and when combined with focus movements using the piezo positioner, the focus positions can be matched at the edges of adjacent strips. These advantages become even more important when the strip width is increased.

Both focus position and tilt can be measured by performing an X-Z scan at several Y positions along each strip before scanning, with the detector tilt set at zero. An X-Z scan can be performed by moving microscope objective 115 in the Z direction using piezo positioner 120 (or alternatively, by moving specimen 400 or linear detector array 425 in the Z direction), while storing a series of line images across the strip using the linear detector. Each line image is segmented into several line segments, and the spatial frequency of the image calculated for each segment. Since the in-focus image is that with the highest spatial frequencies and best contrast, it is then possible to calculate the best focus position for each segment, which allows the tilt angle for the detector and the focus position for the microscope objective to be calculated and stored at each of several Y positions along the strip. It is important that several segments are measured across the width of each line image, in order to ensure that all parts of the object line are in focus, and some segments of the object line are not in the air above the specimen, which could happen if focus measurements were made only at the centre and the two ends of the line. This procedure is repeated for several positions in the scan (Y) direction, and the results stored as a focus and tilt map to be used while scanning. Both focus position and tilt can be adjusted during scan using the focus and tilt map. The focus positions of the edge of the strip can be stored and matched with the edge of the next strip when the focus and tilt measurements for that strip are measured later.

Figure 5:
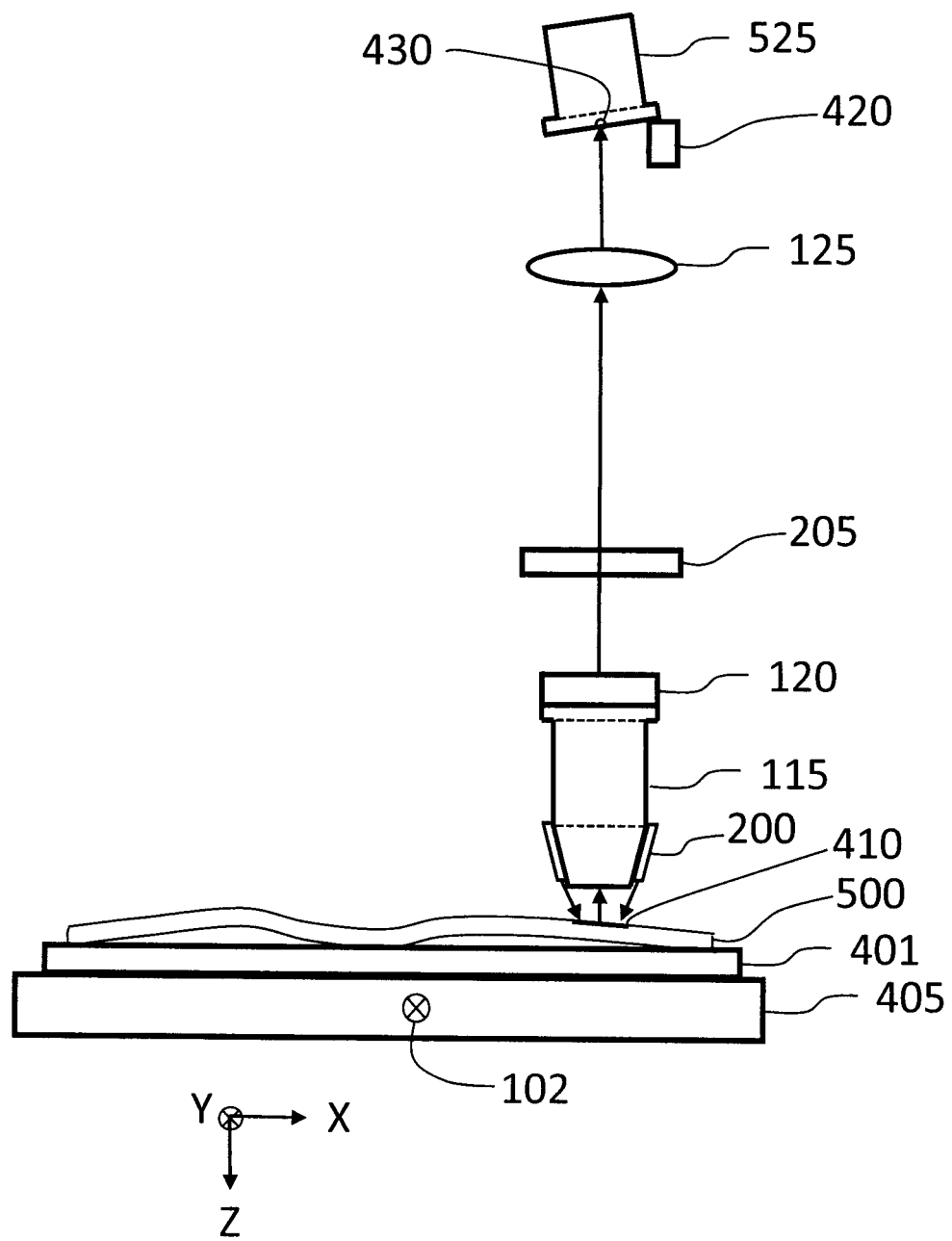
FIG. 5 is a schematic view of a fluorescence scanner with a detector array tilted about the scan direction.

FIG. 5 shows a slide scanner for fluorescence imaging that is a third embodiment of this invention. A tissue specimen 500 (or other specimen to be imaged in fluorescence) mounted on microscope slide 401 is illuminated from above by illumination source 200. In fluorescence imaging the illumination source is usually mounted above the specimen (epifluorescence) so that the intense illumination light that passes through the specimen is not mixed with the weaker fluorescence emission from the specimen, as it would be if the illumination source were below the specimen. {Several other optical combinations can be used for epifluorescence illumination. For example, illumination light can be injected into the microscope tube between the microscope objective 115 and emission filter 205, using a dichroic beamsplitter to reflect it down through the microscope objective 115 and onto the specimen 500 (this optical combination is not shown in FIG. 5)}. A narrow wavelength band for the illumination light is chosen to match the absorption peak of the fluorophore in use. Fluorescence emitted by the specimen is collected by infinity-corrected microscope objective 115 which is focused on the specimen by piezo positioner 120. Emission filter 205 is chosen to reject light at the illumination wavelength and to pass the emission band of the fluorophore in use. The microscope objective 115 and tube lens 125 form a real image of the specimen on TDI detector array 525, which can be tilted about tilt axis 430 using piezoelectric pusher 420 (or other tilt mechanism). The long dimension of linear detector array 525 is perpendicular to scan direction 102. Tilt axis 430 is parallel to scan direction 102. An image of the specimen is collected by moving the microscope slide at constant speed using motorized stage 405 in a direction perpendicular to the long dimension of the detector array 525, combining a sequence of equally-spaced line images from the array to construct an image of one strip across the specimen, with strip width equal to the length of object line 410. When one strip is imaged, motorized stage 405 moves the specimen in the X direction a distance equal to the strip width, and a second strip is scanned. This procedure is repeated until the entire area of the specimen (or the area of interest) has been scanned. Strips are then assembled to form a complete image. When a CCD-based TDI array is used, each line image stored in memory is the result of integrating the charge generated in all of the previous lines of the array while the scan proceeds, and thus has both increased signal/noise and amplitude (due to increased exposure time) when compared to the result from a linear array detector. In this third embodiment, the computer 440 (shown in FIG. 4, not shown in FIG. 5) controls motorized stage 405, piezoelectric pusher 420, and piezo positioner 120, and collects data from detector array 525. In addition to controlling all of the electromechanical parts of the fourth embodiment scanner, the computer 440 also performs all of the other functions necessary to acquire, store, process and display digital image data.

Figure 6:
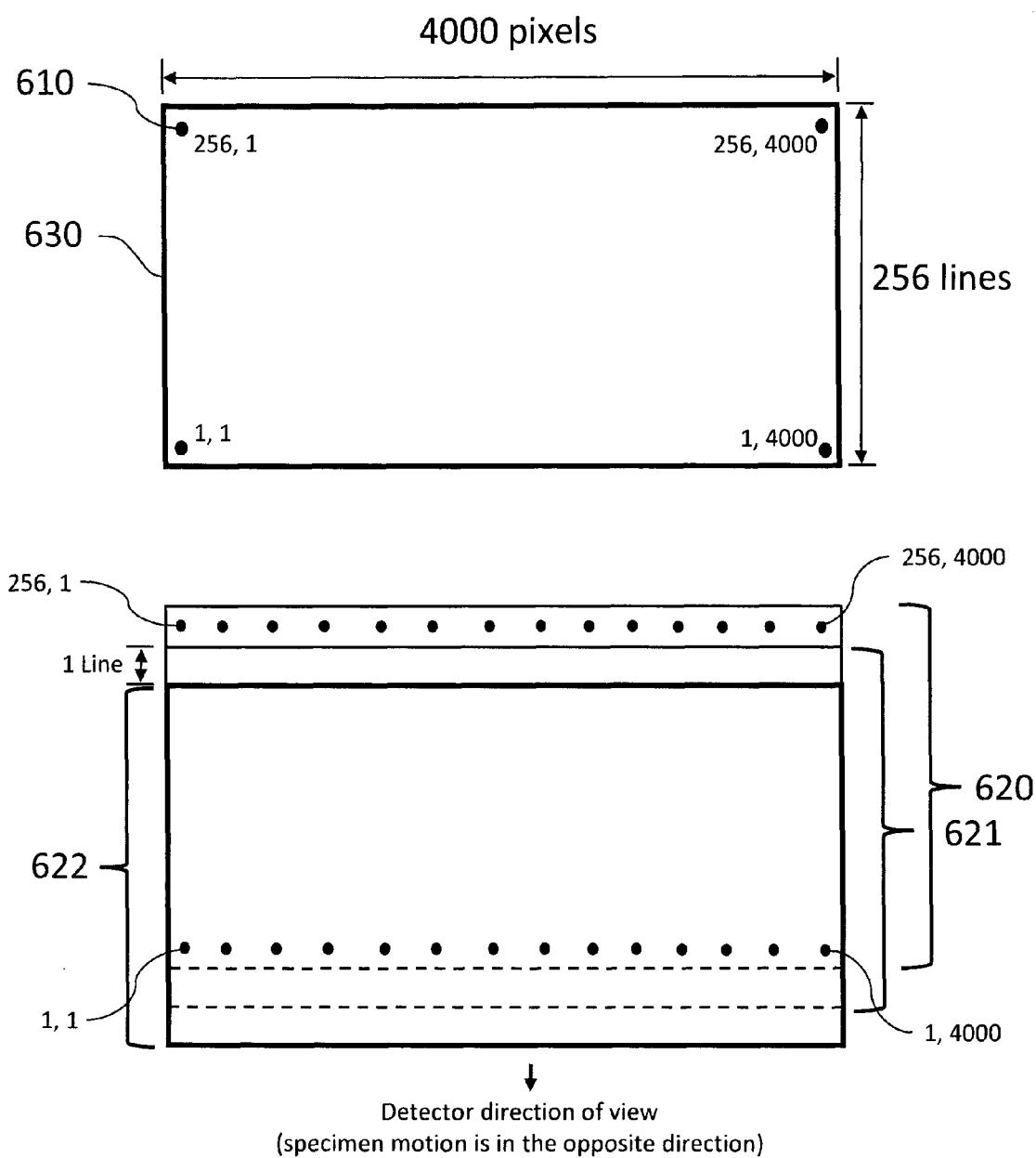
FIG. 6 shows a 256×4000 pixel detector array (top) and three sequential fields of view of the array as the specimen moves during scanning (bottom).

An instrument and method for scanning microscope slides using a CCD or CMOS two-dimensional detector array that adds intermediate image frames acquired every time the microscope slide has moved an incremental distance equal to that between rows of pixels in the final image has been described in U.S. Patent Application Ser. No. 61/427,153, "Pathology Slide Scanner", by A.E. Dixon. The instrument described in that application has all of the advantages of a slide scanner that uses a TDI array, but uses ordinary CCD or CMOS (or other technology) two-dimensional arrays instead. In addition, since the final image is the sum of a large number of intermediate image frames, each intermediate frame being displaced a distance equal to the distance between rows of pixels in the final image, the instrument can have a larger dynamic range than that supported by the detector array, and this increased dynamic range enables multiple fluorophores to be imaged simultaneously using separate detector arrays for each fluorophore, with adjustment for the emission strength (brightness of the image from each fluorophore) after scan is complete. Each line in the final image is the result of adding several exposures of the same line using sequential adjacent lines of pixels in the detector array and then dividing by the number of exposures, or adding the data from each exposure to a data set with a larger dynamic range. For example, one could add 256 exposures from an 8-bit detector into a 16-bit image store for each line in the final image. FIG. 6 shows a 256×4000 pixel detector array 630 (top) and the motion of the field-of-view of the array as the stage moves the specimen during scan (bottom). During scan, intermediate image 620 is stored in the computer 440 (not shown in FIG. 6). Then, after the specimen has moved a distance equal to the distance between rows of pixels in the final image, intermediate image 621 is added to data in the computer, shifted by one row of pixels, followed by intermediate image 622, and so on. Using the array shown in FIG. 6, each pixel in the final strip image stored in computer 440 is the sum of 256 exposures of the same pixel position in the specimen. In this particular example, if the frame grabber produces 8-bit images, the resulting stored image has a dynamic range of 16 bits (each pixel is made up of a sum of 256 exposures where each exposure has a maximum value of 255). The final image will have an exposure time that is 256 times larger than that achieved at the same scan speed using a linear detector array, which is a major advantage when imaging weak fluorophores. This technique is called Moving Specimen Image Averaging (MSIA), and for the purposes of this patent document, this is the definition of Moving Specimen Image Averaging. The fluorescence image of the specimen strip being scanned is stored and adjacent strip images are assembled to produce a final image of the entire specimen. Adjacent strips may be assembled by butting them together, or by collecting overlapping strip images and using feature-matching software for registration.

In a variation of FIG. 5, if TDI detector array 525 is replaced by an ordinary two-dimensional (2D) detector array (not a TDI array), then Moving Specimen Image Averaging can be used to acquire fluorescence image strips as described above. This is a fourth embodiment of this invention. Both focus position and tilt can be measured by performing a Z-scan at several Y positions along each strip before scanning, with the detector tilt set at zero. With the detector parallel to the scan plane, a Z-scan can be performed by moving the microscope objective in the Z direction using the piezo positioner to a series of equally-spaced positions in Z, while storing the resulting series of 2D images, each of which has the same width as the scan strip, using the 2D detector (or alternatively, a Z-scan can be performed by moving either the detector or the specimen in the Z direction). This results in a 3D image stack at each Y position, and if the detector used as an example in the description above is used, this image stack contains 256×4000×N pixels, where N is the number of positions in Z at which each exposure is made. Each of the long, thin images in the stack can be segmented into several short segments, and the spatial frequency of the image calculated for each segment. Since the in-focus image is that with the highest spatial frequencies and best contrast, it is then possible to calculate the best focus position for each segment, which allows the tilt angle for the detector and the focus position for the microscope objective to be calculated and stored at each of several Y positions along the strip. This procedure is repeated for several positions in the scan (Y) direction, and the results stored as a focus and tilt map to be used while scanning. Both focus position and tilt can be adjusted during scan using the focus and tilt map. The focus positions of the edge of the strip can be stored and matched with the edge of the next strip when the focus and tilt measurements for that strip are measured later. This focus and tilt map can be used for imaging by controlling detector tilt about the scan direction (as shown in FIG. 5).

A scanner using Moving Specimen Image Averaging has a major cost advantage over one using a TDI detector, since ordinary 2D arrays are much less expensive than TDI arrays, and the electronic signals for controlling MSIA exposures are usually available from the stage controller used for controlling stage motion in a scanning stage microscope. The same detector used for scanning can be used for measuring focus and tilt to produce a focus and tilt map of the strip before scanning, and a 3D image of a region of interest can be acquired by using the instrument as a tiling microscope. When used as a tiling microscope, the exposure time can be set to whatever time is required for the fluorophore being imaged, since it is not set by the scan speed as it is while scanning along the length of the strip.

We claim:

1. An instrument for scanning a large microscope specimen on a specimen holder, the instrument comprising a light source and at least one lens that focuses light from the specimen onto a detector array, the specimen holder being located on a scanning stage, the detector array being dynamically tilted about a scan direction during a scan to maintain focus across a width of a scan strip as the scan proceeds, the instrument having means to focus axially.

2. The instrument as claimed in claim 1 wherein a degree of tilt of the detector array about the scan direction varies during the scan, as required to maintain the focus.

3. The instrument as claimed in claim 2 wherein the specimen has an object plane that corresponds to an image plane in which the detector array is situated and on which a real image of the object plane is formed.

4. The instrument as claimed in claim 1 wherein the instrument has a means for determining prior to scanning a required tilt and focus and variation in tilt required to maintain the focus during the scan.

5. The instrument as claimed in claim 4 wherein the means for determining is capable of maintaining focus relative to the specimen across a width of a scan strip as the scan proceeds.

6. The instrument as claimed in claim 1 wherein the detector array is a linear detector array.

7. The instrument as claimed in claim 1 wherein the instrument is used for fluorescence imaging and the detector array is a 2D detector array configured for Moving Specimen Image Averaging.

8. The instrument as claimed in claim 1 wherein the instrument is used for fluorescence and the detector array is a TDI detector array.

9. The instrument as claimed in claim 1 wherein the instrument has a microscope objective and tube lens as at least one lens, the detector array being tilted with respect to the scan plane about a Y axis that is in a plane of the specimen holder and is parallel to a direction of motion of the specimen holder along a Y direction.

10. The instrument as claimed in claim 9 wherein the detector array is perpendicular to a row of pixels along the long dimension of the detector array.

11. The instrument as claimed in claim 1 wherein a dynamic tilt of the detector array and a variation thereof is connected to be controlled by a computer during the scan.

12. The instrument as claimed in claim 2 wherein a dynamic tilt of the detector array and a variation thereof is connected to be controlled by a computer during the scan.

13. A method of scanning a large microscope specimen on a specimen holder using an instrument comprising a light source and at least one lens that focuses light from the specimen onto a detector array, the specimen holder being located on a scanning stage, the method comprising dynamically tilting the detector array about a scan direction during a scan to maintain focus relative to the specimen across a width of a scan strip as the scan proceeds, while focusing the instrument relative to the specimen axially.

14. The method of scanning a large microscope specimen as claimed in claim 13 including the step of varying a degree of tilt of the detector array about the scan direction during the scan, as required to maintain the focus.

15. The method of scanning a large microscope specimen as claimed in claim 13 including the step of moving the scanning stage at constant speed in a direction perpendicular to a long dimension of the detector array, combining a sequence of equally-spaced line images from the array to construct an image of one strip across the specimen, after the one strip is imaged, causing the stage to move the specimen in an X direction a distance equal to a strip width and scanning a second strip, repeating the steps until an entire area of interest of the specimen has been scanned.

16. The method of scanning a large microscope specimen as claimed in claim 15 wherein the area of interest is a whole of the specimen.

17. The method of scanning a large microscope specimen as claimed in claim 14 including the steps of assembling image strips of the strips that are imaged to form a complete image.

18. The method of scanning a large microscope specimen as claimed in claim 15 including the steps of configuring a computer to control the scanning stage, a piezoelectric pusher and a piezo positioner and to collect data from the detector array.

19. The method of scanning a large microscope specimen as claimed in claim 16 including the steps of configuring a computer to acquire, store, process and display digital image data.

20. The method of scanning a large microscope specimen as claimed in claim 13 including the steps of imaging the specimen in fluorescence collecting the fluorescence emitted by the specimen forming a real image of the specimen on a TDI detector array.

21. The method of scanning a large microscope specimen as claimed in claim 13 including the steps of using one of a linear detector, a 2D detector array configured for Moving Specimen Image Averaging and a TDI detector array.

22. The method of scanning a large microscope specimen as claimed in claim 13 including the steps of programming a computer and using the computer to control variation of a degree of tilt of the detector array about the scan direction during the scan to maintain focus relative to the specimen.

* * * * *